(12) United States Patent
Grimm et al.

(10) Patent No.: US 7,950,256 B2
(45) Date of Patent: May 31, 2011

(54) WASHING MACHINE CAPABLE OF MEASURING SURFACE PROPERTIES OF LIQUIDS, AND PROCESS FOR DETECTING SUCH SURFACE PROPERTIES

(75) Inventors: Dieter Grimm, Bretzfeld-Brettach (DE); Robert Huettner, Bochum (DE)

(73) Assignee: Whirlpool Corporation, Benton Harbor, MI (US)

( * ) Notice: Subject to any disclaimer, the term of this patent is extended or adjusted under 35 U.S.C. 154(b) by 978 days.

(21) Appl. No.: 10/595,382

(22) PCT Filed: Oct. 14, 2004

(86) PCT No.: PCT/EP2004/052546
§ 371 (c)(1), (2), (4) Date: Apr. 13, 2006

(87) PCT Pub. No.: WO2005/038120
PCT Pub. Date: Apr. 28, 2005

(65) Prior Publication Data
US 2007/0039357 A1 Feb. 22, 2007

(30) Foreign Application Priority Data
Oct. 16, 2003 (EP) ..................................... 03023569

(51) Int. Cl.
*D06F 39/00* (2006.01)
(52) U.S. Cl. ..................... 68/12.27; 68/12.01; 68/12.02; 68/12.05; 68/12.14; 68/12.19

(58) Field of Classification Search .................. 68/12.01, 68/12.02, 12.05, 12.14, 12.19, 12.27; 8/158
See application file for complete search history.

(56) References Cited

U.S. PATENT DOCUMENTS

| 3,677,069 | A | 7/1972 | Rubin et al. | |
|---|---|---|---|---|
| 6,568,017 | B2 * | 5/2003 | Cheo et al. | 8/158 |
| 6,691,536 | B2 * | 2/2004 | Severns et al. | 68/12.27 |
| 7,310,978 | B2 * | 12/2007 | Hisano | 68/23.1 |

FOREIGN PATENT DOCUMENTS

| DE | 19821148 | * | 11/1999 |
|---|---|---|---|
| DE | 19821148 A1 | | 11/1999 |
| EP | 1 096 051 | * | 5/2001 |
| EP | 1096051 A2 | | 5/2001 |
| EP | 1154255 A2 | | 11/2001 |
| EP | 1156318 A1 | | 11/2001 |
| EP | 1441056 A1 | | 7/2004 |
| GB | 2272454 A | | 5/1994 |
| IT | 1156318 | * | 11/2001 |
| JP | 64022297 | | 1/1989 |
| JP | 2126894 | | 5/1990 |

* cited by examiner

*Primary Examiner* — Michael Barr
*Assistant Examiner* — Jason Heckert

(57) ABSTRACT

A washing appliance, particularly a laundry washer or a dishwasher, comprises a tank (2) for loading washing liquor and items to be washed and control means adapted to carry out a predetermined washing program. It further comprises an inclined drain surface (2a) for collecting a portion of the washing liquor and means (6, 8, 9, 10, 11, 12) for assessing properties of such liquid on the basis of the drainage behavior thereof.

12 Claims, 1 Drawing Sheet

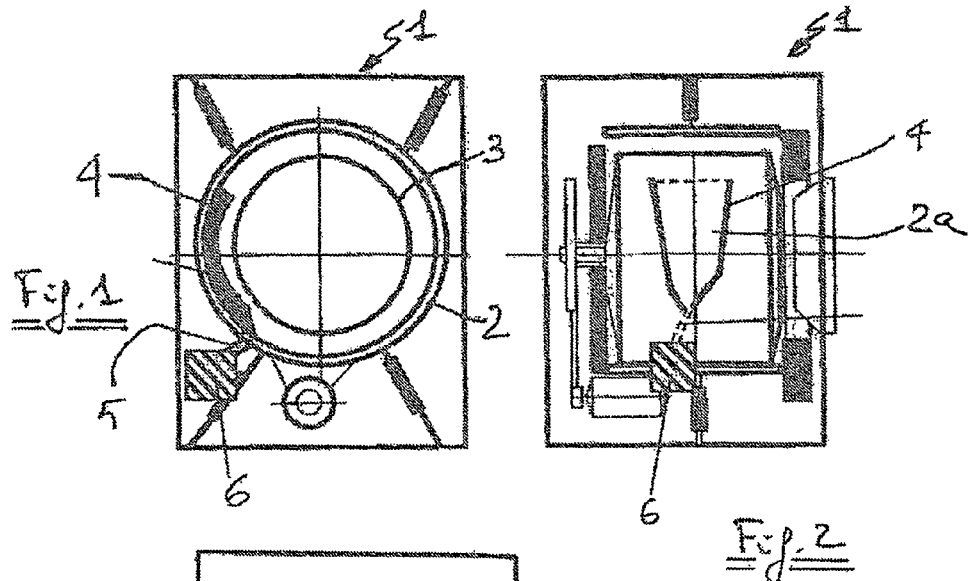
Fig. 1
Fig. 2
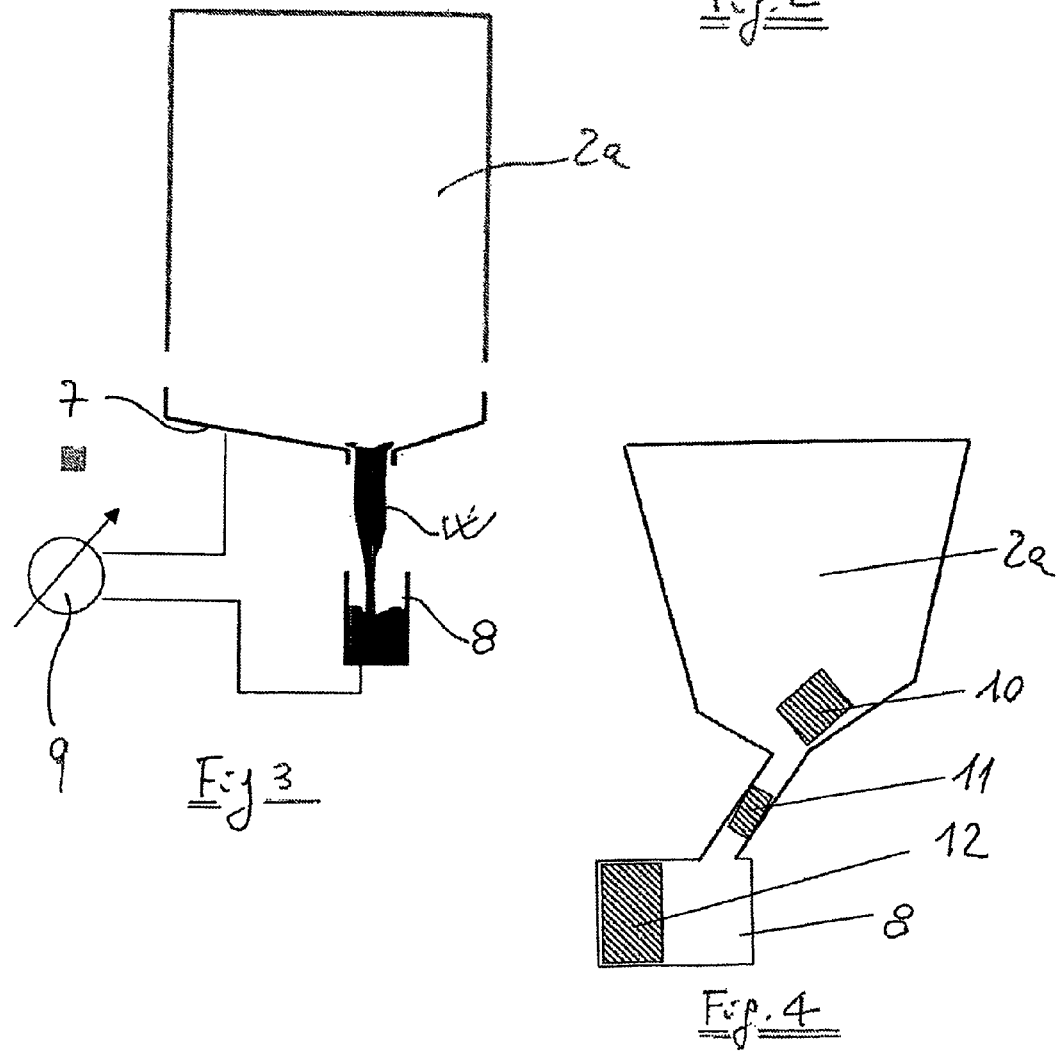
Fig. 3
Fig. 4

WASHING MACHINE CAPABLE OF MEASURING SURFACE PROPERTIES OF LIQUIDS, AND PROCESS FOR DETECTING SUCH SURFACE PROPERTIES

The present invention relates to a washing appliance, particularly a washing machine or a dishwashing machine, comprising a tank for loading washing liquor and items to be washed and control means adapted to carry out a predetermined washing program.

It is well known that in modern washing appliances there is a trend of adjusting the program chosen by the user on the basis of the actual working condition of the machine. Therefore some known washing appliances have sensors for assessing the electrical conductivity of the washing liquor, which is related to the detergent concentration therein, or the turbidity of the washing liquor, which is related to the amount of soil therein, or other working parameters. Another opportunity for assessing parameters of the washing liquor and, consequently, of the actual washing condition, is to check how the liquid, admixed with a cleaning agent, laundry detergent, or dishwashing detergent, performs from a Theological point of view. Knowledge of the mechanical properties of the cleansing liquid is thus of importance, since a major share of the cleansing process consists of mechanical interactions, e.g., transport of water up to the fabric, wetting, distribution, transport of the liquid and laundry detergent/active laundering substances contained therein away from the fabric, etc., with the item to be cleaned. The general dependence of the physical and chemical parameter surface tension and pH on laundry-detergent concentration is already known. However, it is not known or disclosed the demand imposed on the necessary sensors and metrological instrumentation. Known measurement methods (discussed in German and European patents DE 3 303940, DE 2 917859, DD 217557, EP 1 154255, EP 1 063340, 1 063339 and EP 0 760472), such as rise-height measurements, bubble-pressure methods, or tensiometers, suffer from various disadvantages. For example, the rise-height measurements for determining surface tension proposed in German Patent No. DE 3 303940 invariably measure a compound parameter composed of contact angle and surface tension. Either of these latter parameters affects the other and both are variously affected by surfactant laundering substances, and thus incompletely describe the mechanical properties of the medium involved, since its behaviour, in particular its dynamic behaviour (such as that described by its viscosity) will not be determined. Another major disadvantage of the rise-height method described is its susceptibility to surface contaminants in cases where permanent cleansing cannot be guaranteed, which represents a major hindrance in the case of household appliances for which no facilities for external interventions are available. The fuzz and lint solid matter, and foreign particulate present in every wash solution rapidly lead to formation of deposits, difficult-to-remove stains, and surface modifications that directly affect measurements. Such contaminating effects are also known in the case of the bubble-pressure method, where the capillary tube employed is highly susceptible to contamination. European patent application EP 1 154 255 A2 attempts to take account of this by inducting the liquid to be measured into a suction tube, in which measurement takes place, using vacuum. Once measurement has been concluded, the level of the liquid is reduced This method requires a highly elaborate mechanical setup and requires a device for generating a vacuum. The patent also points out the problems that can arise when the bubble-pressure method, as described in European patents EP 1 063 340 A1 or EP 1 063 339 A1, is employed. German patent DD 217 557 states that the surface tension is useful for describing and controlling the laundering process, but makes no detailed statements regarding the manners in which they are to be measured or measurement results are to be analysed.

The applicant has discovered that if the parameters of the washing liquor are determined by measuring how the washing liquor performs on a well defined surface (surface of a sensor) situated in the earth's gravitational field, that is by measuring and evaluating its drainage behaviour, the reliability of such assessment is increased surprisingly. This drainage behaviour is a process that is characterised by convolutions of the transport of cleansing liquid to the item (the surface of, e.g., a fabric in a washing machine) to be cleaned, its distribution over the item, surface, its dwell period there, its wetting of the item surface, and its transport away from the item to be cleaned. Observation and measure of this behaviour allows, in essence, determining the changing mechanical properties of the cleansing liquid during the entire program of the machine, or the effects of the associated process control that occur, for example, in conjunction with a dispensing or diluting device.

European patent application 03001274 filed by the same applicant shows a specific application of the above-mentioned way of assessing parameters of the washing liquor, wherein the drain behaviour of the washing liquid is measured at the drum by a capacity measurement. To achieve this, electrodes of defined size are attached to the drum wall. The capacity of the electrodes changes over time during the draining process of the film. In this application, the electrodes are attached to the reservoir wall without further additional means.

One object of the present invention is to provide different, cheaper and more reliable measuring methods that can be used for the analysis of the drain behaviour. Another object of the present invention is to provide a special design of the drain surfaces (for example at the inner wall of the drum) and special drain devices that are connected to the measuring instruments.

The special design of the drain surfaces according to the invention permits the use of measuring concepts that are totally new in this combination. To provide a combination of a drain device, drain surfaces and a measuring method is a further object of the present invention.

In order to be able to characterise liquids based on their properties while they are in the form of films on surfaces and, in particular, their mechanical properties while they are in the form of films on surfaces, a surface situated in the earth's gravitational field is wet in a defined manner. Upon conclusion of the wetting process, the characteristics of the wet surface are known from the physical and geometric boundary conditions that apply and may be determined by various measurement methods, where the surface is arranged in the earth's gravitational field such that the wetting film tends to drain off. Wetting is followed by a pause of a predetermined duration in order to allow time for the film to drain off. Drainage of the liquid film (wetted surface) may then be determined by using various measurement devices that will be described in the embodiments of the invention. The wetting of the surface and the pause of a defined duration may be repeated many times. Drainage of the liquid is determined by the physical and chemical properties of the liquid, the inclination of the surface in the earth's gravitational field, the properties of the material involved, and its surface roughness. If the properties of the wetted surface (its inclination, geometry, the material involved, its surface roughness, etc.) are known, then some of the relevant mechanical properties of the liquid may be characterised, based on its drainage behaviour.

The wetted surface should be preferably chosen such that it provides the best possible description of the properties of the liquid sought for various applications, when used in various individual applications. Furthermore, surfaces having various, defined, properties whose drainage behaviours are to be simultaneously determined may be simultaneously wetted, which will allow making simultaneous, parallel, measurements of various properties of the liquid. This sort of measurement provides a number of benefits:

- The resultant redundancy of the measurements may be utilised for verifying the plausibility of the measurements. If, for instance, two surfaces having identical properties are arranged at differing inclinations, the liquid should run off more rapidly from the surface that has the steeper inclination, a fact that may be utilised to check the operation of the sensor employed and/or to calibrate it, normalised to a given medium, e.g., fresh water, over its fill service life.
- Employing surfaces inclined at differing angles allows determining the properties of liquid films over broad dynamic ranges. For example, even in the case of liquid films that run off very rapidly, their properties may be determined with high degrees of differentiation in the case of surfaces that have slight inclinations, for the purpose of, e.g., describing rinsing processes.
- The drainage behaviours of surfaces may be strongly dependent upon the local geometry of the areas to which liquids are applied. In the case of measurements employing several surfaces, these surfaces may be distributed over the machine involved such that each surface is situated at a specific location, for example, the lowest point of the vessel involved, the location of the average water level, the location of the highest water level, or similar, in a manner that will yield wetting and drainage properties characteristic of the various individual locations involved. Either information related to extreme measurement conditions or very good averages over the overall characteristics of the machine involved, obtainable by integrating over all signals may be obtained in this manner.

Apart from the possibility of adapting the inclination, the drain surface can also be adapted by other measures, for example by designing the surface texture, such as targeted modelling of the surface roughness.

Due to the general nature of the water movement, the process of surface wetting is subject to strong statistic fluctuations and causes statistically fluctuating signals due to possible incomplete surface wetting, in particular for low water levels. This effect can be decreased by designing the drain surface in such a manner that guide edges, similar to a fimnel, collect the water over a larger area than the actual sensor area. The collected water is supplied to a "measuring system" collectively and therefore averaged integrally. There are now different techniques available as options for the measuring system. These techniques, in combination with the system of the drain surface and/or the drain system, are within the scope of the present invention.

The present invention is described in the following by way of example with reference to the accompanying drawings, in which:

FIG. 1 is a schematic sectioned front view of a washing machine according to the invention, FIG. 2 is a sectioned side view of the washing machine of FIG. 1, FIG. 3 is a schematic view of a component used in the machine according to FIGS. 1 and 2, and FIG. 4 is a schematic view, similar to FIG. 3, according to a second embodiment of the invention.

With reference to the drawings, particularly FIGS. 1 and 2, a washing machine 1 comprises a tub 2 and a rotating drum 3 inside the tub. On the inside surface of the tub 2 there is provided a drain surface 2a with guide edges 4 attached to its sides. Underneath these guide edges, there is a drain 5 placed across the wall of the tub 2, which supplies the collected liquid to the measuring system 6.

Various principles for measuring or quantifying drainage of liquid films in a predetermined time period may be applied either individually or in combination.

The lower edge of the sensor's surface 2a is preferably configured such that the draining liquid film will be diverted, will be collected along one of its edges, and may be trapped there, which may take place in a specially designed vessel where a quantification of the quantity of liquid involved may take place. This quantification may be obtained using various measurement methods, for instance:

- Real-time quantification by means of weight measurements, in which case, the vessel must be weighed using, e.g., a special holder equipped with strain gauges.
- The vessel's fill volume may be determined in real time using, e.g., optical detection of its fill level.
- The lower edge of the sensor's surface 2a is configured such that the draining liquid film leaves its surface at a single location, is subject to gravity and air drag alone, and is also configured such that draining liquid is present in the form of droplets. The number of droplets involved will then be readily determinable using a photoelectric gate.
- The lower edge of the sensor's surface is configured such that the draining liquid film leaves it at a single location, is subject to gravity and air drag alone, and is also configured such that draining liquid forms a continuous stream. This stream may then be utilised for determining the properties of the liquid involved, employing the measurement setup schematically shown in FIG. 3.

Referring to the embodiment of FIG. 3, the drainage surface 2a has a bottom portion 7 which is electrically insulated from the top portion and which serves as first electrode of the measuring system. A collection vessel 8, placed under a discharging opening 7a of the bottom insulated portion 7 of the drainage surface 2a, serves as a second electrode. Both electrodes are connected to an ohmmeter 9 for measuring electrical conductivity of the draining water W.

The essential feature of this measurement setup is that both the surface from which the stream of water W drains and that on which the stream of water lands are configured in the form of electrodes. In the absence of a stream of water, these electrodes are electrically insulated from one another. The stream of water W generates a short circuit that yields a parameter determined by the geometry of the stream of liquid that constitutes a measure of the mechanical properties of the liquid on surfaces, where the behaviour of the stream of liquid as a function of time shortly before it leaves the surface will be a major factor in characterising and quantifying the mechanical properties of the liquid on surfaces. The time that elapses between total wetting of the surface by the liquid and when the stream of water starts draining off the surface represents another parameter quantifying the mechanical properties of the liquid that may be accurately determined with little expenditure of time and effort, since the time when total wetting of the surface has occurred is known (for example, in the case of a washing machine, this will be when the pause preceding reversal of the direction of rotation of its drun 3 commences). An intermittent resistance signal will be received when the stream of water breaks away from the surface. The measurement of the elapsed time may be automatically triggered by that intermittent signal. All the parameters determined through the ohmmeter 9 may be easily correlated to the actual condition of washing or rinsing inside the washing machine 1. For this purpose, the ohmmeter 9 is connected to the electronic control unit (not sown) of the washing machine in order to adjust the program in view of the actual condition, in order to optimise the washing/rinsing cycle and to save water, detergent and energy.

Other major conclusions may be obtained from measurements conducted over the remainder of the drainage process which, in certain cases, may also involve a continuous stream draining off for a short period, where the time intervals between droplets that drain off and droplet size represent major factors in descriptions of the mechanical properties of the liquid or liquid film involved. Droplet size may be determined from weight or volume measurements or optical measurements of droplet size (diameter). A special device must provide that analysis can start only once the aforementioned triggering signal has been received. The times that elapse between individual droplets that drain off may be determined from the pressure or volume signals. Another option for measuring drainage behaviour would be optical determinations employing photoelectric gates. The arrangements of their light sources and detectors may be chosen such that their vertical axes are inclined relative to the paths of droplets, which will allow employing the transmitted signals and reflected signals for signal analysis, due to the differences in the refractive indices of air and the liquid involved.

Another conductive or capacitive method for measuring the drainage of liquid films is shown with reference to FIG. 4. According to such embodiment, the electrodes must be preferably positioned according to a certain pattern. The kind of the electrodes must be adapted to the conditions for a capacitance or conductivity measurement The ideal way to achieve this is by attaching an electrode 10 to the drum inside. This permits a direct measurement of the conductivity. Indirect measurement of the conductivity is also possible by using inductive measuring instruments, where the electrodes are mounted outside the tub wall. All the above systems for assessing parameters of the liquid used in the washing appliance according to the invention can be used either during the washing process or during the rinsing process. In the first case the detergent concentration will be much higher than in the second case. For sake of simplicity, with the term "washing liquor" we mean the liquid inside the washing appliance, independently on the actual detergent concentration.

The invention claimed is:

1. A washing appliance comprising:
a tank for loading washing liquor and items to be washed and having a side wall defining an inside surface with a low portion where liquid will collect;
a drum rotatably mounted within the tank;
a controller carrying out a predetermined washing program;
spaced guide edges projecting inwardly from the inside surface of a side of the tank and extending vertically downwardly from a vertical position above a middle portion of the tank toward the low portion below the middle portion such that the guide edges converge toward the low portion to define therebetween an inclined drain surface provided on the inside surface of the tank to funnel a portion of the washing liquor along the inclined drain surface; and
at least one measuring instrument in communication with the inclined drain surface and assessing mechanical properties of such washing liquor funneled along the inclined drain surface on the basis of a drainage behavior thereof.

2. The washing appliance according to claim 1, wherein the inclined drain surface consists of a defined area limited by the guide edges and the drain to the at least one measuring instrument.

3. The washing appliance according to claim 1, wherein more than one inclined surface is used, arranged at different angles.

4. The washing appliance according to claim 3, further comprising another measuring instrument and wherein signals from the measuring instruments correspond to different surfaces at different angles and are used for calibration or for internal reference of the measuring instruments.

5. The washing appliance according to claim 2, wherein a determination of an amount of a draining film of washing liquor is performed over a defined time period in the at least one measuring instrument, the at least one measuring instrument comprising a storage vessel, which can be emptied in defined time intervals and is fed by the draining washing liquor.

6. The washing appliance according to claim 2, wherein a determination of an amount of a draining film of washing liquor is performed over a defined time period by an optical fill level gauge, the at least one measuring instrument containing a storage vessel which can be emptied in defined time intervals and is fed by the draining washing liquor.

7. The washing appliance according to claim 2, wherein a lower end of the drain surface is arranged in such a manner that the draining washing liquor leaves it in a drop form and a measured quantity is determined from a number of the drops per time unit and their size.

8. The washing appliance according to claim 2, wherein an end of the drain surface is designed in such a manner that a draining washing liquor film gathers to a continuous fluid stream, and a conductivity of this stream is determined by a suitable measuring instrument.

9. The washing appliance according to claim 8, wherein a bottom portion serves as a first electrode and a collection vessel serves as a second electrode and that a parameter based on a geometry of the washing liquor, flowing from a discharge of the bottom portion to the vessel, is determined by a conductivity measurement.

10. The washing appliance according to claim 2 or 9, wherein a capacitive sensor is used for measuring the drainage behavior and electrodes of the capacitive sensor are positioned outside the tank.

11. The washing appliance according to claim 2, wherein a capacitive sensor is used for measuring the drainage behavior and electrodes of the capacitive sensor are positioned at a lower edge of the drain surface, in the drain, or in a collecting vessel in the at least one measuring instrument itself 12. The washing appliance according to claim 11, wherein the kind of the electrodes is designed in such a manner that a conductive measurement can be performed too.

* * * * *